United States Patent [19]

Foguet et al.

[11] Patent Number: 4,728,655

[45] Date of Patent: Mar. 1, 1988

[54] SULFONAMIDINES, PROCESS FOR THE PRODUCTION THEREOF AND PHARMACEUTICAL COMPOSITIONS CONTAINING THE SAME

[75] Inventors: Rafael Foguet; Luis Anglada; Josep Castello; Aurelio Sacristan; Jose Ortiz, all of Barcelona, Spain

[73] Assignee: Ferrer Internacional S.A., Barcelona, Spain

[21] Appl. No.: 724,784

[22] Filed: Apr. 18, 1985

[30] Foreign Application Priority Data

| Apr. 18, 1984 | [ES] | Spain | 531764 |
| Apr. 19, 1984 | [ES] | Spain | 532242 |
| Jun. 18, 1984 | [ES] | Spain | 533948 |
| Jun. 18, 1984 | [ES] | Spain | 533949 |
| Jan. 24, 1985 | [ES] | Spain | 540190 |
| Jan. 24, 1985 | [ES] | Spain | 540192 |
| Mar. 12, 1985 | [ES] | Spain | 541189 |
| Mar. 12, 1985 | [ES] | Spain | 541190 |

[51] Int. Cl.$^4$ .................. C07D 417/12; A61K 31/445
[52] U.S. Cl. ..................... 514/326; 514/331; 514/357; 514/363; 514/365; 514/397; 514/399; 514/471; 546/209; 546/231; 546/246; 548/136; 548/193; 548/336; 548/342; 549/471

[58] Field of Search .............. 546/209, 231, 246; 548/136, 193, 336, 342; 549/491; 514/331, 357, 363, 365, 397, 399, 471, 326

Primary Examiner—Robert T. Bond
Attorney, Agent, or Firm—Michael J. Striker

[57] ABSTRACT

Sulfonamidine is disclosed of the general formula (I):

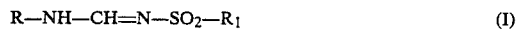

$$R-NH-CH=N-SO_2-R_1 \qquad (I)$$

wherein R is a group selected from 2-[[(5-methyl-1H-imidazole-4-yl)methyl]thio]ethyl], 2-[[[5-[(dimethylamino)methyl]-2-furanyl]methyl]thio]ethyl, 2-[[[2-[(aminoiminomethyl)amino]-4-thiazolyl]methyl]thio]ethyl] or 3-[3-(1-piperidinylmethyl)phenoxy] propyl and R$_1$ is alkyl; or a phenyl group optionally substituted by alkyl, halogen, nitro, alkoxy, alkanoylamino, carboxylic acid, alkoxycarbonyl, dialkylamino, alkylsulphonyl, alkylsulphonylamino or alkylthio; or 1,3,4-thiadiazole-2-yl substituted by alkanoylamino, and the pharmaceutically acceptable salts thereof, as well as a process for preparing these compounds and pharmaceutical compositions containing the same. These compounds have antiulcer activity and can be used in the treatment of peptic ulcers and other pathologies caused or stimulated by gastric acidity.

18 Claims, No Drawings

SULFONAMIDINES, PROCESS FOR THE PRODUCTION THEREOF AND PHARMACEUTICAL COMPOSITIONS CONTAINING THE SAME

BACKGROUND OF THE INVENTION

This invention concerns antihistamines in general, and more particularly, those which block the $H_2$-receptors.

It is known that histamine, a physiological compound which is found in living organisms, may be bound to certain specific receptors for exerting its activity. Two types of histamine receptors have been identified so far: $H_1$-receptors, in which the action of histamine is blocked by conventional antihistamine drugs, for example, mepyramine (Ash and Schild: Bri. J. Pharmac, Chemother., 27, 427–39, 1966); and $H_2$-receptors, in which the action of histamine is blocked by cimetidine (Black et al: Nature, 23(6), 385–90, 1972). The blockade of histamine activity by $H_2$-receptors results in the inhibition of gastric acid secretion, thus making the compounds with this potency effective for the treatment of peptic ulcers and other pathologies caused or stimulated by gastric acidity.

However, the known compounds are not always satisfactory and there is always a need for improved pharmaceuticals of this nature.

SUMMARY OF THE INVENTION

These and other objects are attained by new sulfonamidine of the general formula (I):

$$R-NH-CH=N-SO_2-R_1 \quad (I)$$

wherein R is 2-[[(5-methyl-1H-imidazole-4-yl)methyl]-thio]ethyl, 2-[[[5-[(dimethylamino)methyl]-2-furenyl]-methyl]thio]ethyl, 2-[[[2-[(aminoiminomethyl)amino]-4-thiazolyl]methyl]thio]ethyl or 3-[3-(1-piperidinylmethyl)phenoxy]propyl and $R_1$ is either a small group having 4 carbon atoms at most, preferably, methyl, or a phenyl group optionally substituted by a small alkyl group having 4 carbon atoms at most, preferably methyl or ethyl, a halogen atom, preferably chlorine or bromine, a nitro group, an alkoxy group having 4 carbon atoms at most, preferably methoxy, a small alkanoylamino group having 4 carbon atoms at most, preferably acetylamino, a carboxylic acid group, an alkoxycarbonyl group, the alkoxy group of which contains 4 carbon atoms at most, preferably methoxycarbonyl, a dialkylamino group, the alkyl group of which contains 4 carbon atoms each at most, preferably dimethylamino, an alkylsulphonyl group, the alkyl group of which contains 4 carbon atoms at most, preferably methylsulphonyl, an alkylsulphonylamino group, the alkyl group of which contains 4 carbon atoms at most, preferably methylsulphonylamino or an alkylthio group, the alkyl group of which contains 4 carbon atoms at most, preferably methylthio; or a 1,3,4-thiadiazole-2-yl substituted by a small alkanoylamino group having 4 carbon atoms at most, preferably acetylamino, and its pharmaceutically acceptable salts.

The compounds of the present invention may be obtained, for example, according to the following reaction sequences:

Reaction Sequence 1

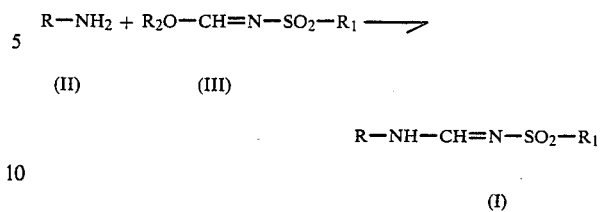

where R in (II) is as defined for (I) and $R_2$ in (III) is an alkyl group having 4 carbon atoms at most and ethyl is preferred, $R_1$ in (III) is as defined for (I).

The reaction is carried out at room temperature in a medium selected from an alkanol having 1 to 4 carbon atoms, preferably methanol or ethanol. When the amines of the general formula (II) are not used in free form but salified with mineral acids, the acid is conveniently neutralized by addition of a base, preferably an alkali or earth alkaline hydroxide, most preferably potassium hydroxide, before reacting with the corresponding sulphonyl-formidates (III).

The intermediates of the general formula (III) are prepared from respective sulfonamides by reacting with triethyl orthoformiate according to a convention method as described by Setter (Chem. Ber., 102(5), 1641–2, 1969).

Reaction Sequence 2

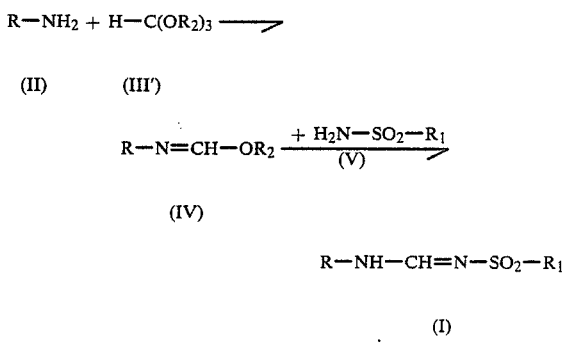

where R—$NH_2$ is as defined for the Reaction Sequence 1 and $R_2$ *in (III')* *is as defined for (III')*, R and $R_2$ in (IV) and $R_1$ in (V) are as defined in precedent structures.

The reaction between the amines of the general formula (II) and the orthoformates of the general formula (III') leads, under suitable temperature conditions (100°–120° C.), to the intermediate imidates of the general formula (IV). The reaction occurs at ease by the excess orthoformate, so that it is not necessary to use any solvent because of the liquid composition of these orthoformates. While the suitable temperature conditions for the formation of the intermediate imidates of the general formula (IV) range from 100° to 120° C., the reaction also occurs over a wide range of temperature, namely, between 65° C. and boiling point of the mixture. The applicants have discovered that the imidates of the general formula (IV) thus obtained, subject to prior evaporation of the excess orthoformate and without purification, can react with the sulfonamides of the general formula (V), in a solvent selected from an alkanol having 4 carbon atoms at most, preferably methanol or ethanol, and under mild temperature conditions, such as room temperature, thus obtaining the sulfonamidines of the present invention. When the amines of the general formula (II) are not used in free form, but are salified with mineral acids, it is convenient, before undertaking the reaction with the orthoformates of the general formula (III'), to neutralize the acid by addition of a base, i.e., preferably an alkaline or earth alkaline hydroxide, most preferably potassium hydroxide, dissolved in an alkanol having 4 carbon atoms at most, preferably methanol, followed by removal by filtration of the formed inorganic salt and subsequent separation of solvent by vacuum evaporation.

The intermediate imidates of the general formula (IV), new compounds too, also fall within the scope of the present invention.

After preparation of the compounds according to the invention, their salts with respective acids can also be obtained by reaction in an inert medium, i.e., preferably selected from water, an alkanone or an alkanol having 4 carbon atoms at most. Thus, for example, acetone, ethanol or mixtures therefor with water. When the carboxylic acid function is found in the compounds of the general formula (I), their precursors salified with alkaline metals are generally used as starting material, this directly obtaining the alkaline salts of the compounds of the present invention.

The compounds of the present invention have an effective property for antagonizing histamine $H_2$-receptors, thus becoming useful in therapy as acid secretion inhibitors. It is known that histamine, a physiological compound which is found in living organisms, may be bound to certain specific receptors for exerting its activity. Two types of histamine receptors have been identified so far: $H_1$-receptors, in which the action of histamine is blocked by conventional antihistaminic drugs, for example, mepyramine (Ash and Schild: Brit. J. Pharmac. Chemother., 27, 427-39, 1966); and $H_2$-receptors, in which the action of histamine is blocked by cimetidine (Black et al: Nature, 23(6), 385-90, 1972). The blockade of histamine activity by $H_2$-receptors results in the inhibition of gastric acid secretion, thus making the compounds with this potency effective for the treatment of peptic ulcer and other pathologies caused or stimulated by gastric acidity.

The blocking qctivity of histamine $H_2$-receptors was tested in Sprague-Dawley male rats weighing 345±38 g. Animals which were subjected to a 24-hour hydric diet were tracheotomized under ethyl carbamate anesthesia (1 ml/100 g, 10% w/V i.p.). After cannulating the esophagus and stomach from duodenum, the gastric contents were drained. Then the esophageal cannual was connected to a peristaltic pump, under prior passage over a thermostatic batch at 37° C., and 1/800N sodium hydroxide solution in water flowed through. The cannula from the stomach was connected by a tube leading to a Ph-meter electrode, and the readings were graphically recorded. pH increase occurring by perfusion of the sodium hydroxide solution at 1.6 ml/min. rate is antagonized by continuous infusion of histamine hydrochloride through a catheter implanted in the right femoral vein (0.0552 mg/min/kg, 2 ml/hour). After calibrating the pH, test drugs are quickly injected into the right femoral vein. Under these conditions, the activities, expressed at $ED_{50}$, of some compounds according to the present invention, are determined and set forth as follows, with cimetidine being employed for purposes of comparison:

TABLE 1

| Compound | Activity ($ED_{50}$, μmol/kg) |
|---|---|
| Ex. 1, hydrogen maleate | 0.70 |
| Ex. 2, hydrogen maleate | 1.77 |
| Ex. 3, hydrogen maleate | 1.12 |
| Ex. 4, hydrogen maleate | 0.61 |
| Ex. 5, hydrogen maleate | 0.75 |
| Cimetidine | 5.60 |

The compounds of the present invention, when mixed with pharmaceutically acceptable carrier, can be administered by the oral route in the form of tablets, capsules, dragees, syrups, solution, and the like, by injectable route and by rectal route, at daily doses ranging from 5 to 2000 mg.

By way of a non-limitative illustration within the essence of the invention, the described processes for preparing these compounds are set forth in the following description of the preferred embodiments.

DESCRIPTION OF THE PREFERRED EMBODIMENTS

EXAMPLE 1

N-p-toluen-sulphonyl-N'-[2-[[[2-[(aminoiminomethyl)amino]-4-thiazolyl]methyl]thio]ethyl]formamidine To a solution of 7 g of [4-[[(2-aminoethyl)thio]methyl]-2-thiazolyl]guanidine dihydrochloride (prepared according to U.S. Pat. No. 4,165,378) in 70 ml of methanol, 34.9 ml of 1.45M methanol potassium hydroxide are added at 0° C. To the resulting solution, 5.22 g of ethyl N-p-toluen-sulphonyl-formimidate dissolved in 30 ml of methanol are added at room temperature. The mixture is then stirred for 1 hour, filtered off and the solvent is removed by distilling at reduced pressure. The formed residue is purified by dissolving in 150 ml of ethyl acetate and 70 ml of water. Then it is acidulated with 3N hydrochloric acid till pH 2. The organic phase is cast aside and the aqueous phase is basified in the presence of 150 ml of ethyl acetate with saturated sodium carbonate solution. The organic phase is washed with water, dried over magnesium sulphate and evaporated to dryness. 6.06 g. of N-p-toluen-sulphonyl-N'-[2-[[[2-(aminoiminomethyl)amino-4-thiazolyl]methyl]thio]ethyl]formamidine are obtained.

Melting point: 143°-145° C.

One basic group (anhydrous medium): 99.7%.

| Elemental analysis: | C | H | N |
|---|---|---|---|
| Found | 43.63 | 5.08 | 20.58 |
| Calculated | 43.67 | 4.89 | 20.37 |
| Sulphur (Schoniger) | Found | Calculated | |
| | 23.03 | 23.31 | |

IR Spectrum: characteristic bands at 1610 cm$^{-1}$ (C=N, st).

$^1$H-NMR (DMSO-d$_6$)δ=2.3 (3H, s, φ—CH$_3$), 2.54 (2H, t, —S—CH$_2$—CH$_2$), 3.3 ((2H, m, —$\overline{CH_2}$—CH$_2$—NH—), 3.52 (2H, s, het—CH$_2$—S—), 6.36 (1H, s, thiazole), 6.8 (4H, wide, guanidine), 7.5 (4H, m, aromatic), 8.1 (1H, d, —NH—C$\underline{H}$=N), 8.86 (1H, wide —NH—CH=).

The hydrogen maleate is prepared by dissolving the obtained product in 45 ml of acetone and adding 2.7 g of maleic acid dissolved in 20 ml of acetone, 6.3 g of N-p- toluensulphonyl-N'-[2-[[[2-[(aminoiminomethyl)amino]-4-thiazolyl]methyl]thio]ethyl]formamidine hydrogen maleate are obtained.

Melting point: 164°–167° C.

One basic group (anhydrous medium): 99.7%.

| Elemental analysis: | C | H | N |
|---|---|---|---|
| Found | 42.81 | 4.55 | 15.4 |
| Calculated | 43.17 | 4.58 | 15.19 |

| Sulphur (Schoniger) | Found | Calculated |
|---|---|---|
| | 17.66 | 18.19 |

IR Spectrum: characteristic bands at 1600 cm$^{-1}$ (C=N, st).

$^1$H-NMR (DMSO-d$_6$) δ=2.34 (3H, s, φ—CH$_3$), 2.58 (2H, t, —S—CH$_2$—CH$_2$—), 3.4 (2H, m, —CH$_2$—CH$_2$—NH—), 3.68 (2H, s, het—CH$_2$—S), 6.1 (2H, s, —CH=CH—), 7 (1H, s, thiazole), 7.5 (4H, m, aromatic), 8.15 (5H, wide, —NH—CH=N—, guanidine), 8.0 (1H, wide, —NH—CH=).

EXAMPLE 2

N-benzenesulphonyl-N'-[2-[[[2-[(aminoiminomethyl)amino]-4-thiazolyl]methyl]thio]ethyl]formamidine Following the steps described in Example 1, N-benzenesulphonyl-N'-[2-[[[2-[(aminoiminomethyl)amino]-4-thiazolyl]methyl]thio]ethyl]formamidine is obtained.

Melting point: 152°–154° C.

One basic group (anhydrous medium); 99.8%.

| Elemental analysis: | C | H | N |
|---|---|---|---|
| Found | 43.2 | 4.79 | 20.96 |
| Calculated | 42.2 | 4.55 | 21.09 |

| Sulphur (Schoniger): | Found | Calculated |
|---|---|---|
| | 23.4 | 24.13 |

IR Spectrum: characteristic bands at 1600 cm$^{-1}$ (C=N, st).

$^1$H-NMR (DMSO-d$_6$) δ=2.6 (2H, t, —S—CH$_2$—CH$_2$—), 3.38 (2H, m, —CH$_2$—CH$_2$—NH), 3.54 (2H, s, het—CH$_2$—S), 6.42 (1H, s, thiazole), 6.84 (4H, wide, guanidine), 7.6 (5H, m, aromatic), 8.16 (1H, s, —NH—CH=N—), 8.9 (1H, wide, —NH—CH=).

In the same manner as described in Example 1, N-benzenesulphonyl-N'-[2-[[[2-[(aminoiminomethyl)amino]-4-thiazolyl]methyl]thio]ethyl]formamidine hydrogen maleate is obtained.

Melting point: 160°–163° C.

One basic group (anhydrous medium): 99.9%.

| Elemental analysis: | C | H | N |
|---|---|---|---|
| Found | 42.95 | 4.79 | 15.82 |
| Calculated | 42.01 | 4.31 | 16.33 |

| Sulphur (Schoniger): | Found | Calculated |
|---|---|---|
| | 17.86 | 18.69 |

IR Spectrum: characteristic bands at 1600 cm$^{-1}$ (C=N), st). $^1$H-NMR (DMSO-d$_6$): δ=2.58 (2H, t, —S—CHHd 2—CH$_2$), 3.4 (2H, m, —CH$_2$—CH$_2$—NH—), 3.68 (2H, s, het—CH$_2$—S), 6.1 (2H, s, —CH=CH—), 7 (1H, s, thiazole), 7.64 (5H, m, aromatic), 8.12 (5H, wide, —NH—CH=N, guanidine), 8.9 (1H, wide, —NH—CH=).

EXAMPLE 3

N-methansulphonyl-N'-[2-[[[2-[(aminoiminomethyl)amino]-4-thiazolyl]methyl]thio]ethyl]formamidine Following the steps described in Example 1, N-methansulphonyl-N'-[2-[[[2-[(aminoiminomethyl)amino]-4-thiazolyl]methyl]thio]ethyl]formamidine hydrogen maleate is obtained.

Melting point: 201°–205° C.

One basic group (anhydrous medium): 102.8%.

| Elemental analysis | C | H | N |
|---|---|---|---|
| Found | 35.24 | 4.75 | 18.11 |
| Calculated | 34.50 | 4.46 | 18.57 |

| Sulphur (Schoniger): | Found | Calculated |
|---|---|---|
| | 20.5 | 21.25 |

IR Spectrum: characteristic bands at 1615 cm$^{-1}$ (C=N, st).

$^1$H-NMR (DMSO-d$_6$): δ=2.5 (2H, t, —S—CH$_2$—CH$_2$—), 2.7 (3H, s, —SO$_2$—CH$_3$), 3.25 (2H, m, —CH$_2$—CH$_2$—NH—), 3.6 (2H, s, het—CH$_2$—S), 5.9 (2H, s, —CH=CH—), 6.85 (1H, s, thiazole, 7.9 (5H, wide, guanidine, —NH—CH=N), 8.5 (1H, wide, —NH—CH=).

The hydrochloride is prepared by dissolving the base in absolute ethanol and adding a stoichiometric quantity of saturated hydrogen chloride solution in ethanol, and the formed hydrochloride precipitates with ethyl ether.

Melting point: 110°–112° C.

One acid group (anhydrous medium): 96.2%.

| Elemental analysis: | C | H | N |
|---|---|---|---|
| Found | 28.91 | 4.72 | 21.95 |
| Calculated | 28.99 | 4.60 | 22.54 |

| | Found | Calculated |
|---|---|---|
| Sulphur (Schoniger). | 9.78 | 9.51 |
| Chlorine (Schoniger) | 24 | 25.79 |

IR Spectrum: characteristic bands at 1610 cm$^{-1}$ (C=N, st). $^1$H-NMR (DMSO-d$_6$) δ=2.54 (2H, t, —S—CH$_2$—CH$_2$), 2.84 (3H, s, —SO$_2$—CH$_3$), 3.4 (2H, m, —CH$_2$—CH$_2$—NH—), 3.78 (2H, s, het—CH$_2$—S), 7.16 (1H, s, thiazole), 7.98 (1H, d, —NH—CH=N—), 8.32 (4H, wide, guanidine), 8.85 (1H, wide, —NH—CH=).

EXAMPLE 4

N-p-nitrobenzene-sulphonyl-N'-[2-[[[2-(aminoiminomethyl)amino]-4-thiazolyl]methyl]thio]ethyl formamidine Following the steps described in Example 1, N-p-nitrobenzenesulphonyl-N'-[2-[[[2-[(aminoiminomethyl)amino]-4-thiazolyl]methyl]thio]ethyl]formamidine hydrogen maleate is obtained.

Melting point: 167°–170° C.

One basic group (anhydrous medium): 102.8%.

| Elemental analysis: | C | H | N |
|---|---|---|---|
| Found | 39.76 | 4.24 | 16.95 |
| Calculated | 38.63 | 3.78 | 17.52 |

| Sulphur (Schoniger): | Found | Calculated |
|---|---|---|
| | 16.45 | 17.19 |

IR Spectrum: characteristic bands at 1605 cm$^{-1}$ (C=N, st); 1340, 1140 cm$^{-1}$ (SO$_2$, st).

$^1$H-NMR (DMSO-d$_6$): δ=2.6 (2H, t, —S—C$\underline{H}$$_2$—CH$_2$—), 3.45 (2H, m, —CH$_2$—C$\underline{H}$$_2$—NH—), 3.7 (2H, s, het-C$\underline{H}$$_2$—S), 6.1 (2H, s, —C$\underline{H}$=C$\underline{H}$—), 7 (1H, s, thiazole), 8.2 (9H, m, aromatic, guanidine, —N$\underline{H}$—C$\underline{H}$=N), 9.2 (1H, wide, —N$\underline{H}$—CH=).

As described in Example 3, the hydrochloride is obtained.

Melting point: 90°–93° C.

| Elemental analysis: | C | H | N |
|---|---|---|---|
| Found | 33.65 | 4.28 | 19.00 |
| Calculated | 35.03 | 3.78 | 20.43 |

| | Found | Calculated |
|---|---|---|
| Sulphur (Schoniger): | 18.3 | 20.04 |
| Chlorine (Schoniger) | 6.7 | 7.39 |

IR Spectrum: characteristic bands at 1610 cm$^{-1}$.

$^1$H-NMR (DMSO-d$_6$): δ=2.6 (2H, t, —S—C$\underline{H}$$_2$—), 3.4 (2H, m, —CH$_2$—C$\underline{H}$$_2$—NH—), 3.7 (2$\underline{H}$, s, het—CH$_2$—S—), 7.06 (1H, s, thiazole), 8.2 (9H, m, aromatic, guanidine, —NH—C$\underline{H}$=N—), 9.35 (1H, wide, —N$\underline{H}$—CH=).

EXAMPLE 5

N-p-chlorobenzene-sulphonyl-N'-[2-[[[2-[(aminoiminomethyl)amino]-4-thiazolyl]methyl]thio]ethyl]formamidine Following the steps described in Example 1, N-p-chlorobenzenesulphonyl-N'-[2-[[[2-[(aminoiminomethyl)amino]-4-thiazolyl]methyl]thio]ethyl]formamidine recrystallizing from acetonitrile is obtained.

Melting point: 75°–78° C.

One basic group (anhydrous medium): 103%.

| Elemental analysis: | C | H | N |
|---|---|---|---|
| (calculated for C$_{14}$H$_{17}$ClN$_6$O$_2$S$_3$.CH$_3$CN) | | | |
| Found | 41.20 | 4.62 | 19.9 |
| Calculated | 40.54 | 4.25 | 20.69 |

| | Found | Calculated |
|---|---|---|
| Sulphur (Schoniger) | 19.99 | 20.29 |
| Chlorine (Schoniger) | 7.52 | 7.48 |

IR Spectrum: characteristic bands at 1610 cm$^{-1}$ (C=N, st).

$^1$H-NMR (DMSO-d$_6$): δ=2.02 (2H, s, CH$_3$—CN), 2.56 (2H, t, S—CH$_2$—CH$_2$—), 3.38 (2H, m, —CH$_2$—C$\underline{H}$$_2$—NH—), 3.52 (2$\underline{H}$, s, het—CH$_2$—S—), 6.38 (1H, s, thiazole), 6,78 (4H, wide, guanidine), 7.6 (4H, m, aromatic), 8.12 (1H, s, —NH—C$\underline{H}$=N—), 9.4 (1H, wide, —N$\underline{H}$—CH=).

In the same manner as described in Example 1, N-p-chlorobenzenesulphonyl—N'-[2-[[[2-[(aminoiminomethyl)amino]-4-thiazolyl]methyl]thio]ethyl]formamidine hydrogen maleate is obtained.

Melting point: 160°–162° C.

One basic group (anhydrous medium): 98.4%.

| Elemental analysis: | C | H | N |
|---|---|---|---|
| Found | 40.04 | 4.16 | 15.35 |
| Calculated | 39.40 | 3.86 | 15.32 |

| | Found | Calculated |
|---|---|---|
| Sulphur (Schoniger) | 17.3 | 17.53 |
| Chlorine (Schoniger) | 5.97 | 6.40 |

IR Spectrum: characteristic bands at 1600 cm$^{-1}$ (C=N, st).

$^1$H-NMR (DMSO-d$_6$): δ=2.56 (2H, t, —S—C$\underline{H}$$_2$—CH$_2$), 3.4 (2H, m, —CH$_2$—C$\underline{H}$$_2$—NH—), 3.66 (2$\underline{H}$, s, het—CH$_2$—S), 6.1 (2H, s, —C$\underline{H}$=C$\underline{H}$—), 7 (1H, s, thiazole), 7.56 (4H, m, aromatic), 8.02 (4$\underline{H}$, wide, guanidine), 8.15 (1H, d, —NH—C$\underline{H}$=—N—), 9.75 (1H, wide, —N$\underline{H}$—CH=).

EXAMPLE 6

N-p-toluen-sulphonyl-N'-[2-[[[5-[(dimethylamino)methyl]-2-furanyl]methyl]thio]ethyl]formamidine To a solution of 2.14 g of 5-[[(2-aminoethyl)thio]methyl]N,N-eimethyl-furanmethamine (prepared according to Belgian Pat. No. 857,388) in 40 ml of absolute ethanol, 2.27 g of ethyl N-p-toluen-sulphonyl-formimidate dissolved in 20 ml of absolute ethanol are dropwise added at room temperature and stirring. The mixture is kept under stirring for 1 hour and the ethanol is removed by distilling at reduced pressure. The obtained residue is purified by dissolving in 40 ml of ethyl acetate and 25 ml of water. Then it is acidulated with 3N hydrochloric acid till pH2. The organic phase is cast aside and the aqueous phase is basified in the presence of 20 ml of ethyl acetate with 1N sodium hydroxide till pH9. The organic phase is washed with water, dried over magnesium sulphate and evaporated to dryness. The obtained residue is chromatographied under 60 silicagel column and chloroform:methanol (8:2) as eluent. 2.15 g (oil product) of N-p-toluen-sulphonyl-N'-[2-[[[5-[(dimethylamino)methyl]2-furanyl]methyl]thio]ethyl]formamidine are obtained.

One basic group (anhydrous medium): 95.8%.

| Elemental analysis: | C | H | N |
|---|---|---|---|
| Found | 55.06 | 5.91 | 8.74 |
| Calculated | 54.66 | 6.37 | 10.62 |

| Sulphur (Schoniger) | Found | Calculated |
|---|---|---|
| | 15.5 | 16.27 |

IR Spectrum: characteristic bands at 1610 cm$^{-1}$ (C=N, st).

$^1$H-NMR (CDCl$_3$): δ=2.1 (6H, s, (CH$_3$)$_2$N—), 2.25 (3H, s, φ—CH$_3$), 2.55 (2H, t, —S—C$\underline{H}$$_2$—CH$_2$—), 3.2 (4H, m, het—C$\underline{H}$$_2$—S—, —CH$_2$—C$\underline{H}$$_2$—NH—), 3.5 (2H, s, =N—C$\underline{H}$$_2$—het), 5.9 (2H, s, furane), 7.3 (4H, m, aromatic), 7.95 (1H, s, —NH—C$\underline{H}$=N—).

EXAMPLE 7

N-p-chlorobenzene-sulphonyl-N'-[2-[[[5-[(dimethylamino)methyl]-2-furanyl]methyl]thio]ethyl]formamidine Following the steps described in Example 6, N-p-chlorobenzene-sulphonyl-N'-[2-[[[5-[(dimethylamino)-methyl]2-furanyl]methyl]thio]ethyl]formamidine is obtained.

Melting point: 93°–96° C.

One basic group (anhydrous medium): 99.5%.

| Elemental analysis: | C | H | N |
|---|---|---|---|
| Found | 49.17 | 5.37 | 9.87 |
| Calculated | 49.09 | 5.33 | 10.10 |

IR Spectrum: characteristic bands at 1605 cm$^{-1}$ (C=N, st), 1310, 1145 cm$^{-1}$ (SO$_2$, st).

$^1$H-NMR (CDCl$_3$): δ=2.20 (6H, s, (C$\underline{H}_3$)$_2$N—), 2.64 (2H, t, —S—C$\underline{H}_2$—CH$_2$—), 3.34 (4H, m, het—C$\underline{H}_2$—S, —CH$_2$—C$\underline{H}_2$—NH—), 3.6 (2H, s, =N—C$\underline{H}_2$—het), 6.07 (2H, s, furane), 7.6 (H, m, aromatic), 8.18 (1H, s, —NH—C$\underline{H}$=N—).

EXAMPLE 8

N-benzene-sulphonyl-N'-[2-[[[5-[(dimethylamino)methyl]-2-furanyl]methyl]thio]ethyl]formamidine Following the steps described in Example 6, N-benzenesulphonyl-N'-[2-[[[5-[(dimethylamino)methyl]-2-furanyl]methyl]thio]ethyl]formamidine is obtained.
Melting point: 83°–85° C.
One basic group (anhydrous medium): 98.3%.

| Elemental analysis: | C | H | N |
|---|---|---|---|
| Found | 53.39 | 5.91 | 10.93 |
| Calculated | 53.52 | 6.08 | 11.01 |
| Sulphur (Schoniger): | Found | | Calculated |
| | 16.65 | | 16.81 |

IR Spectrum: characteristic bands at 1600 cm$^{-1}$, (C=N, st), 1315, 1145 cm$^{-1}$ (SO$_2$, st).

$^1$H-NMR (CDCl$_3$): δ=2.2 (6H, s, (C$\underline{H}_3$)$_2$N—), 2.65 (2H, t, —S—C$\underline{H}_2$—CH$_2$—), 3.34 (4H, m, het—C$\underline{H}_2$—S, —CH$_2$—C$\underline{H}_2$—NH—), 3.6 (2H, s, =N—C$\underline{H}_2$—het), 6.06 (2H, s, furane), 7.5 (3H, m, aromatic), 7.85 (2H, m, aromatic), 8.15 (1H, s, —NH—C$\underline{H}$=N—).

EXAMPLE 9

N-methan-sulphonyl-N'-[2-[[[5-[(dimethylamino)methyl]-2-furanyl]methyl]thio]ethyl]formamidine Following the steps described in Example 6, N-methansulphonyl-N'-[2-[[[5-[(dimethylamino)methyl]-2-furanyl]methyl]thio]ethyl]formamidine (oil product) is obtained.
One basic group (anhydrous medium): 96.4%.

| Elemental analysis: | C | H | N |
|---|---|---|---|
| Found | 45.83 | 6.25 | 11.95 |
| Calculated | 45.12 | 6.63 | 13.15 |
| Sulphur (Schoniger): | Found | | Calculated |
| | 19.5 | | 20.07 |

IR Spectrum: characteristic bands at 1610 cm$^{-1}$ (c=N, st), 1340, 1130 cm$^{-1}$ (SO$_2$, st).

$^1$H-NMR (CDCl$_3$): δ=2.2 (6H, s, (C$\underline{H}_3$)$_2$N—), 2.7 (2H, t, —S—C$\underline{H}_2$—CH$_2$—), 2.85 (3H, s, —SO$_2$—C$\underline{H}_3$), 3.3 (4H, wide, het—C$\underline{H}_2$—S, —CH$_2$—C$\underline{H}_2$—NH—), 3.62 (2H, s, =N—C$\underline{H}_2$—het), 6 (2H, s, furane), 7.9 (1H, s, —NH—C$\underline{H}$=N—).

EXAMPLE 10

N-benzene-sulphonyl-N'-[3-[3-(1-piperidinylmethyl)phenoxy]propyl]formamidine

To a solution of 2.13 g of 3-[3-(1-piperidinylmethyl)phenoxy]-1-propanamine (prepared according to British Pat. No. 2,023,133) in 20 ml of absolute ethanol, 2.48 g of ethyl N-benzene-sulphonyl-formamidate dissolved in 20 ml of absolute ethanol are dropwise added under room temperature and stirring. The mixture is kept stirring for 1 hour and the ethanol is removed by distillation at reduced pressure. The obtained residue is purified by dissolving in 40 ml of ethyl acetate and 25 ml of water, then it is acidulated with 3N hydrochloric acid till pH2. The organic phase is cast aside and the aqueous phase is basified in the presence of 20 ml of sodium acetate with 1N sodium hydroxide till pH6. The organic phase is washed with water, dried over magnesium sulphate and evaporated to dryness. The obtained residue is chromatographied by 60 silicagel column with chloroform:methanol (8:2) as eluent. 1.8 g of N-benzenesulphonyl-N'-[3-[3-(1-piperidinylmethyl)phenoxy]propyl]formamidine are obtained.
Melting point: 80°–82° C.
One basic group (anhydrous medium): 99.97%.

| Elemental analysis: | C | H | N |
|---|---|---|---|
| Found | 63.35 | 6.81 | 9.80 |
| Calculated | 63.59 | 7.03 | 10.11 |
| Sulphur (Schoniger) | Found | | Calculated |
| | 7.74 | | 7.72 |

IR Spectrum: characteristic bands at 1600 cm$^{-1}$ (C=N, st), 1320, 1145 cm$^{-1}$ (SO$_2$, st).

$^1$H-NMR (CDCl$_3$): δ=1.46 (6H, wide, piperidine), 2.0 (2H, m, —CH$_2$—C$\underline{H}_2$CH$_2$), 2.34 (4H, wide, piperidine), 3.42 (2H, s, het—C$\underline{H}_2$—φ—), 3.5 (2H, m, —CH$_2$—C$\underline{H}_2$—CH$_2$—NH—), 4.0 (2H, O—C$\underline{H}_2$—CH$_2$—CH$_2$—), 6.9 (4H, m, aromatic), 7.5 (3H, m, aromatic), 7.9 (2H, m, aromatic), 8.3 (1H, d, —NH—C$\underline{H}$=N—).

EXAMPLE 11

N-p-chlorobenzene-sulphonyl-N'-[2-[3-(1-piperidineylmethyl)phenoxy]propyl]formamidine Following the steps described in Example 10, N-p-chlorobenzene-sulphonyl-N'-[3-[3-(1-piperidinylmethyl)phenoxy]propyl]formamidine is obtained.
Melting point: 75°–79° C.
One basic group (anhydrous medium): 93.07%.

| Elemental analysis: | C | H | N |
|---|---|---|---|
| Found | 58.30 | 6.15 | 8.81 |
| Calculated | 58.72 | 6.27 | 9.34 |
| | Found | | Calculated |
| Sulphur (Schoniger); | 7.06 | | 7.12 |
| Chlorine (Schoniger) | 8.4 | | 7.9 |

IR Spectrum: characteristic bands at 1640 cm$^{-1}$ (C=N, st), 1330, 1140 cm$^{-1}$ (SO$_2$, st).

$^1$H-NMR (DMSO-d$_6$): δ=1.4 (6H, wide, piperidine), 1.88 (2H, m, —CH$_2$—C$\underline{H}_2$—CH$_2$—), 2.3 (4H, wide, piperidine), 3.4 (4H, wide, het—C$\underline{H}_2$—φ—, —CH$_2$—C$\underline{H}_2$—CH$_2$—NH), 3.92 (2H, t, O—C$\underline{H}_2$—CH- 2—CH$_2$—), 6.82 (4H, m. aromatic), 7.2 (1H, m, aromatic), 7.55 (4H, m, aromatic), 8.2 (1H, d, —NH—C$\underline{H}$=N—).

EXAMPLE 12

N-methan-sulphonyl-N'-[3-[3-(1-piperindinylmethyl)-phenoxy]propyl]formamidine

Following the steps described in Example 10, N-methansulphonyl-N'-[3-[3-(1-piperidinylmethyl)-phenoxy]propyl]formamidine (oil product) is obtained.

IR Spectrum: characteristic bands at 1610 cm$^{-1}$ (C=N, st), 1340, 1130 cm$^{-1}$ (SO$_2$, st).

$^1$H-NMR (DMSO-d$_6$): δ=1.46 (6H, wide, piperidine), 2.06 (2H, m, —CH$_2$—CH$_2$), 2.35 (4H, wide, piperidine), 2.88 (3H, s, —SO$_2$—CH$_3$), 3.40 (2H, s, het—CH$_2$—φ), 3.52 (2H, m, —CH$_2$—CH$_2$—CH$_2$—NH), 4.01 (2H, t, —O—CH$_2$—CH$_2$—CH$_2$), 7.0 (4$\underline{H}$, m, aromatic), 8.14 (1H, d, —NH—C$\underline{H}$=N—).

EXAMPLE 13

N-p-toluen-sulphonyl-N'-[3-[3-(1-piperidinylmethyl)-pheonxy]propyl]formamidine

Following the steps described in Example 10, N-p-toluensulphonyl-N'-[3-[3-(1-piperidinylmethyl)phenoxy]propyl]formamidine is obtained. N-p-toluen-sulphonyl-N'-[3-[3-(1-piperidinylmethyl)phenoxy]propyl]formamidine hydrogen oxolate is obtained by dissolving equimolecular quantities of the base and oxalic acid in ethanol and allowing to crystallize under cooling.

Hydrogen oxolate

Melting point: 135°–140° C.

One basic group (anhydrous medium): 96.6%.

| Elemental analysis: | C | H | N |
|---|---|---|---|
| Found | 57.21 | 6.27 | 7.76 |
| Calculated | 57.79 | 6.40 | 8.09 |
| Sulphur (Schoniger): | Found | Calculated | |
| | 6.2 | 6.17 | |

IR Spectrum: characteristic bands at 1600 cm$^{-1}$ (C=N, st).

$^1$H-NMR (DMSO-d$_6$): δ=1.58 (6H, wide, piperidine), 1.9 (2H, m, —CH$_2$—CH$_2$—CH$_2$—), 2.92 (4H, wide piperidine), 3.34 (2H, m, —CH$_2$—CH$_2$—CH$_2$—NH—), 3.94 (2H, t, —O—CH$_2$—CH$_2$—CH$_2$—), 4.06 (2H, s, het—CH$_2$—φ—), 7 (4$\underline{H}$, m, aromatic), 7.25 (2H, m, aromatic), 7.60 (2H, m, aromatic), 8.12 (1H, d, —NH—C$\underline{H}$=N—), 9 (1H, wide, —NH—CH—).

EXAMPLE 14

N-p-chlorobenzene-sulphonyl-N'-[2-[[(5-methyl-1H-imidazole-4-yl)methyl]thio]ethyl]formamidine To a solution of 2.44 g of 2-[[(5-methyl-1H-imidazole-4-yl)methyl]thio]ethanamine (prepared according to British Pat. No. 1,338,169) in 50 ml of methanol, 13.3 ml of 1.45M methanol potassium hydroxide are added at 0° C. To the resulting solution, 2.47 g of ethyl N-p-chloro-benzene-sulphonylformimidate are added at room temperature and stirring. The mixture is kept under stirring for 1 hour at room temperature, then filtered off and the solvent is removed by distillation at reduced pressure. The formed residue is purified by dissolving in 50 ml of ethyl acetate and 25 ml of water. Then, it is acidulated with 3N hydrochloric acid till pH2. The organic phase is cast aside and the aqueous phase is basified in the presence of 50 ml of ethyl acetate with 1N sodium hydroxide till pH8. The organic phase is washed with water, dried over magnesium sulphate and evaporated to dryness. 2.3 g (oily product) of N-p-chlorobenzene-sulphonyl-N'-[2-[[(5-methyl-1H-imidazole-4-yl)methyl]thio]ethyl]formamidine are obtained.

One basic group (anhydrous medium): 93.9%.

| Elemental analysis: | C | H | N |
|---|---|---|---|
| Found | 45.65 | 4.9 | 14.16 |
| Calculated | 45.09 | 4.60 | 15.03 |
| Sulphur (Schoniger): | 8.92 | 9.51 | |

IR Spectrum: characteristic bands at 1600 cm$^{-1}$ (C=N, st).

$^1$H-NMR (DMSO-d$_6$): δ=2.1 (3H, s, CH$_3$—het), 2.6 (2H, t, —S—CH$_2$—CH$_2$), 3.44 (2H, t, —CH$_2$—CH$_2$—NH), 3.6 (2$\underline{H}$, s, het—CH$_2$—S), 7.6 (5H, m, aromatic), 8.2 (1H, s, —NH— C$\underline{H}_2$=N—).

EXAMPLE 15

N-benzene-sulphonyl-N'-[2-[[(5-methyl-1H-imidazole-4-yl)methyl]thio]ethyl]formamidine Following the steps described in Example 14, N-benzenesulphonyl-N'-[2-[[(5-methyl-1H-imidazole-4-yl)methyl]thio]ethyl]formamidine is obtained.

Melting point: 48°–51° C.

One basic group (anhydrous medium): 98.9%.

| Elemental analysis: | C | H | N |
|---|---|---|---|
| Found | 49.62 | 5.79 | 16.15 |
| Calculated | 49.68 | 5.36 | 16.65 |
| Sulphur (Schoniger): | Found | Calculated | |
| | 18.18 | 18.95 | |

IR Spectrum: characteristic bands at 1600 cm$^{-1}$ (C=N, st).

$^1$H-NMR (CDCl$_3$): δ=2.14 (3H, s, CH$_3$—het), 2.65 (2H, t, —S—CH$_2$—CH$_2$—), 3.5 (2H, m, —CH$_2$—CH$_2$—NH—), 7.44 (3H, m, aromatic), 7.82 (3H, m, aromatic, —NH—C$\underline{H}$=N), 8.26 (1H, s, imidazole).

EXAMPLE 16

N-p-toluen-sulphonyl-N-'-[2-[[[2-[(aminoiminomethyl)amino]-4-thiazolyl]methyl]thio]ethyl]formamidine To 7 g of [4-[[(2-aminoethyl)thio]methyl]-2-thiazolyl]guanidine dihydrochloride (prepared according to U.S. Pat. No. 4,165,378) suspended in 70 ml of methanol, 34.9 ml of 1.45M methanol potassium hydroxide are added at 0° C. To the resulting suspension, 5.22 g of ethyl N-p-toluenpsulphonyl-formimidate dissolved in 30 ml of methanol are added at room temperature. The mixture is then stirred for 1 hour, filtered off and the solvent is removed by distilling at reduced pressure. The formed residue is purified by dissolving in 150 ml of ethyl acetate and 70 ml of water. Then, it is acidulated with 3N hydrochloric acid till pH2. The organic phase is case aside and the aqueous phase is basified in the presence of 150 ml of ethyl acetate with saturated sodium carbonate solution. The organic phase is washed with water, dried over magnesium sulphate and evaporated to dryness. 6.06 g of N-p-toluensulphonyl-N'-[2-[[[2-[(aminoiminomethyl)amino]-4-thiazolyl]methyl]thio]ethyl]formamidine are obtained.

The hydrochloride is prepared by mixing the base in absolute ethanol and to the resulting suspension the stoichiometric quantity of saturated solution of hydrogen chloride in ethanol is added, thus precipitating the formed hydrochloride with ethyl ether.

The hydrochloride can also be prepared by mixing the base in water and to the resulting suspension, the stoichiometric quantity of 1N HCl aqueous solution is added, and then the resulting solution is subjected to lyophilization.

In both cases the product shows the following physico-chemical characteristics:

Aid groups (anhydrous medium): 100.6%.

| Elemental analysis: | C | H | N |
|---|---|---|---|
| Found | 40.12 | 4.86 | 18.03 |
| Calculated | 40.13 | 4.72 | 18.72 |

| | Found | Calculated |
|---|---|---|
| Sulphur (Schoniger): | 20.8 | 21.4 |
| Chlorine (Schoniger) | 7.6 | 7.87 |

IR Spectrum: characteristic bands at 1685 cm$^{-1}$ (C=NH$_2$, st); 1610 cm$^{-1}$ (C=N, st), 1330 and 1140 cm$^{-1}$ (SO$_2$, st).

$^1$H-NMR (DMSO-d$_6$): δ=2.34 (3H, s, φ—CH$_3$), 2.58 (2H, t, —S—CH$_2$—CH$_2$—), 3.4 (2H, m, —CH$_2$—CH$_2$—NH—), 3.70 (2H, s het—CH$_2$—S—), 7.05 (1H, s, thiazole), 7.47 (4H, c, aromatic), 8.1 (1H, d, —NH—CH=N—), 8.32 (4H, s, guanidine) 9.06 (1H, wide, —NH—CH=).

EXAMPLE 17

N-methan-sulphonyl-N'-[3-[3-(1-piperidinylmethyl)-phenoxy]propyl]formamidine

To a solution of 2.13 g of 3-[3-(1-piperidinylmethyl)-phenoxy]-1-propanamine (prepared according to British Pat. No. 2,023.133) in 20 ml of absolute ethanol, 1.75 g of ethyl N-methan-sulphonyl-formimidate dissolved in 20 ml of absolute ethanol are dropwise added under room temperature and stirring. The mixture is kept stirring for 1 hour and the ethanol is removed by distillation under reduced pressure. The obtained residue is purified by dissolving in 40 ml of ethyl acetate and 25 ml of water, then it is acidulated with 3N hydrochloric acid till pH2. The organic phase is cast aside and the aqueous phase is basified in the presence of 20 ml of sodium acetate with 1N sodium hydrochloride till pH8. The organic phase is washed with water, dried over magnesium sulphate and evaporated till dryness. The obtained residue is chromatographied by 60 silicagel column will chloroform:methanol (8:2) as eluent. 1.5 g of N-methan-sulphonyl-N'-[3-[3-(1-piperidinyl)phenoxy]propyl]formamidine are obtained.

The hydrogen oxalate is prepared by mixing up equimolecular ethanol solutions of the base and oxalic acid and allowing to crystallize under cooling.

Melting point: 162°-165° C.
Basic group (anhydrous medium): 100.3%.

| Elemental analysis: | C | H | N |
|---|---|---|---|
| Found | 51.91 | 6.22 | 9.24 |
| Calculated | 51.45 | 6.59 | 9.47 |

| Sulphur (Schoniger) | Found | Calculated |
|---|---|---|
| | 7.32 | 7.23 |

IR Spectrum: characteristic bands at 1610 cm$^{-1}$ (C=N, st).

$^1$H-NMR (DMSO-d$_6$): δ=1.60 (6H, wide, piperidine), 1.96 (2H, m, —CH$_2$—CH$_2$—CH$_2$) 2.80 (3H, s, —SO$_2$—CH$_3$), 2.90 (4H, wide, piperidine), 3.40 (2H, m, —CH$_2$—CH$_2$—CH$_2$—NH—), 4 (4H, m, —O—CH$_2$—CH$_2$—CH$_2$—, het—CH$_2$—φ), 7.1 (4H, m, aromatic), 8 (1H, d, —NH—CH—N—), 8.9 (1H, wide, —NH—CH=).

EXAMPLE 18

N-p-acetylaminobenzene-sulphonyl-N'-[2-[[[2-[(aminoiminomethyl)amino]-4-thiazolyl]methyl]thio]ethyl]formamidine This compound is prepared according to Example 16, which shows the following physico-chemical characteristics:

Melting point: 152°-155° C.
1 basic group (anhydrous medium). 93.9%.

| Sulphur (Schoniger: | Found | Calculated |
|---|---|---|
| | 19.8 | 21.1 |

IR Spectrum: characteristic bands at 1650 cm$^{-1}$ (C=O, st); 1605 cm$^{-1}$ (C=N, st).

$^1$H-NMR (DMSO-d$_6$): δ=2.05 (3H, s, —CO—CH$_3$), 2.56 (2H, t, —S—CH$_2$—CH$_2$—), 3.38 (2H, m, —CH$_2$—CH$_2$—NH—), 3.52 (2H, s, het-CH$_2$—S—), 6.38 )1H, s, thiazole), 6.8 (4H, s, guanidine), 7.68 (4H, s, aromatic), 8.08 (1H, s, —NH—CH=N—), 8.86 (1H, wide, —NHCH=), 10.24 (1H, s, φ—NH—CO—CH$_3$).

EXAMPLE 19

N-p-acetylaminobenzene-sulphonyl-N'-[3-[3-(1-piperidinylmethyl)phenoxy]propyl]formamidine This compound is prepared according to Example 17, which shows the following physico-chemical characteristics:

Melting point: 136°-138° C.
1 basic group (anhydrous medium): 98.2%.

| Elemental analysis: | C | H | N |
|---|---|---|---|
| Found | 59.88 | 6.30 | 11.76 |
| Calculated | 60.99 | 6.83 | 11.86 |

| Sulphur (Schoniger): | Found | Calculated |
|---|---|---|
| | 6.61 | 6.78 |

IR Spectrum: characteristic bands at 1670 cm$^{-1}$ (C=O, st), 1605 (C=N, st).

$^1$H-NMR (DMSO-d$_6$): δ=1.39 (6H, wide, piperidine), 1.88 (2H, m, —CH$_2$—CH$_2$—CH$_2$—), 2.27 (2H, wide, piperidine), 3.33 (4H, m, —CH$_2$—CH$_2$—CH$_2$—NH—, het—CH$_2$—φ—), 3.92 (2H, t, —O—CH$_2$—CH$_2$—CH$_2$—), 7 (4H, m, aromatic), 8.1 (1H, s, —NH—CH=N—), 8.85 (1H, wide, —NH—CH=), 10.21 (1H, s, φ—NH—CO—CH$_3$), 7.7 (4H, s, aromatic).

EXAMPLE 20

N-(5-acetyl)amino-1,3,4-thiadiazole-2-yl)sulphonyl-N'-3-3-(1-piperidinylmethyl)phenoxy propyl formamidine This compound is prepared according to Example 17, which shows the following physico-chemical characteristics:

Melting point: 150°-155° C.

One basic group (anhydrous medium): 98.5%.

| Elemental analysis: | C | H | N |
|---|---|---|---|
| Found | 50.34 | 6.01 | 17.02 |
| Calculated | 49.98 | 5.87 | 17.49 |
| Sulphur (Schoniger): | Found | | Calculated |
| | 13.24 | | 13.34 |

IR Spectrum: characteristic bands at 1610 cm$^{-1}$ (C=N, st).

$^1$H-NMR (DMSO-d$_6$): =1.40 (5H, wide, piperidine), 1.94 (2H, m, —CH$_2$—CH$_2$—CH$_2$), 2.20 (3H, s, —CO—CH$_3$), 2.30 (4H, wide, piperidine), 3.36 (4H, m, —CH$_2$—CH$_2$—CH$_2$—NH—, het—CH$_2$—φ), 3.95 (2H, t, —O—CH$_2$—CH$_2$), 7 (4H, m, aromatic), 8.25 (1H, s, —NH—CH=N—).

EXAMPLE 21

N-(5-acetylamino-1,3,4-thiadazole-2-yl)sulphonyl-N'-[2-[[[2-[(aminoiminomethyl)amino]-4-thiazolyl]methyl]thio]ethyl]formamidine This compound is prepared according to Example 16, which shows the following physico-chemical characteristics:

Melting point: 130°–144° C.
One basic group (anhydrous medium): 102%.

| Elemental analysis: | C | H | N |
|---|---|---|---|
| Found | 30.57 | 4.07 | 26.62 |
| Calculated | 31.09 | 3.70 | 27.19 |
| Sulphur (Schoniger): | Found | | Calculated |
| | 26.33 | | 27.66 |

IR Spectrum: characteristic bands at 1610 cm$^{-1}$ (C=N, st).

$^1$H-NMR (DMSO-d$_6$): δ=2.19 (3H, s, —CO—CH$_3$), 2.57 (2H, t, S—CH$_2$—CH$_2$—), 3.45 (2H, m, —CH$_2$—CH$_2$—NH—), 3.55 (2H, s, het—CH$_2$—S—), 6.42 (1H, s, thiazole), 6.80 (4H, wide, guanidine), 8.25 (1H, s, —NH—CH=N—), 9.45 (1H, wide, —NH—CH=).

EXAMPLE 22

N-p-carboxybenzene-sulphonyl-N'-[2-[[[2-[(aminoiminomethyl)amino]-4-thiazolyl]methyl]thio]ethyl]formamidine, potassium salt This compound is prepared according to Example 16, which shows the following physico-chemical characteristics:

Melting point: 160°–170° C.

| Sulphur (Schoniger): | Found | Calculated |
|---|---|---|
| | 18.6 | 20.0 |

IR Spectrum: characteristic bands at 1610 cm$^{-1}$ (C=N, st).

$^1$H-NMR (DMSO-d$_6$): δ=2.63 (2H, t, —S—CH$_2$—CH$_2$—), 3.43 (2H, m, —CH$_2$—CH$_2$—NH—), 3.54 (2H, s, het-CH$_2$—S—), 6.42 (1H, s, thiazole, 7.20 (4H, wide, guanidine), 7.82 (4H, m, aromatic), 8.15 (1H, s, —NH—CH=N—), 9.75 (1H, wide, —NH—CH=).

EXAMPLE 23

N-p-bromobenzene-sulphonyl-N'-[2-[[[2-[(aminoiminomethyl)amino]-4-thiazolyl]methyl]thio]ethyl]formamidine To a suspension of 15.2 g of [4-[[(2-aminoethyl)thio]methyl]-2-thiazolyl]guanidine dihydrochloride (prepared according to U.S. Pat. No. 4,165,378) in 40 ml of methanol, 66.5 ml of 1.66M methanol potassium hydroxide are added at 0° C. To the resulting suspension, 14.6 g of ethyl N-p-bromobenzene-sulphonylformimidate dissolved in 20 ml of methanol are added at room temperature. The mixture is then stirred for 1 hour, filtered off and the solvent is removed by distillation under reduced pressure. The formed residue crystallizes in ethyl acetate to yield 16 g of N-p-bromobenzene-sulphonyl-N'-[2-[[[2-[(aminoiminomethyl)amino]-4-thiazolyl]methyl]thio]ethyl]formamidine.

Melting point: 107°–110° C.
One basic group (anhydrous medium): 99.15%.

| Elemental analysis: | C | H | N |
|---|---|---|---|
| Found | 34.18 | 3.76 | 18.00 |
| Calculated | 35.22 | 3.59 | 17.60 |
| | Found | | Calculated |
| Sulphur (Schoniger): | 19.11 | | 20.15 |
| Bromine (Schoniger): | 15.38 | | 16.74 |

IR Spectrum: characteristic bands at 1605 cm$^{-1}$ (C=N, st).

$^1$-NMR (DMSO-d$_6$): δ=2.58 (2H, t, —S—CH$_2$—CH$_2$), 3.45 (2H, m, CH$_2$—CH$_2$—NH—), 3.55 (2H, s, het—CH$_2$—S—), 6.4 (1H, s, thiazole), 6.8 (4H, wide, guanidine), 7.7 (4H, s, aromatic), 8.15 (1H, s, NH—CH=N), 9 (1H, wide, —NH—CH=).

The hydrochloride is prepared by dissolving the base in absolute ethanol and adding the stoichiometric quantity of ethanol/hydrochloric acid.

The hydrochloride is also prepared by mixing up the base with water and adding stoichiometric quantity of 1M HCl aqueous solution, and then the resulting solution is subjected to lyophylization.

In both cases the product shows the following Nuclear Magnetic Resonance Spectrum:

$^1$H-NMR (DMSO-d$_6$): δ=2.38 (2H, t, —S—CH$_2$—CH$_2$), 3.45 (2H, m, CH$_2$—CH$_2$—NH), 3.7 (2H, s, het—CH$_2$—S), 7.06 (1H, s, thiazole), 7.7 (4H, s, aromatic), 8.12 (1H, d, —NH—CH=N), 8.32 (4H, wide, guanidine), 9.65 (1H, wide, —NH—CH=), 13.15 (1H, wide, guanidine).

The methansulphonate is prepared by mixing up the base with water and adding the stoichiometric quantity of 1M methansulphonic acid in water, and then the resulting solution is subjected to lyophilization.

One basic group (anhydrous medium) 89%.

| Sulphur (Schoniger): | Found | Calculated |
|---|---|---|
| | 20.31 | 22.36 |

$^1$H-NMR (DMSO-d$_6$): δ=2.5 (3H, s, CH$_3$—SO$_3$H), 2.58 (2H, t, —S—CH$_2$—CH$_2$), 3.45 (2M, m, CH$_2$—CH$_2$—NH), 3.7 (2H, s, het—CH$_2$—S), 7.05 (1H, s, thiazole), 7.7 (4H, s, aromatic), 8.15 (1H, d, CH=N), 8.38 (4H, wide, guanidine), 9.3 (1H, wide, —NH—CH=), 13.2 (1H, wide, guanidine).

EXAMPLE 24

N-p-methoxycarbonylbenzene-sulphonyl-N'-[2-[[[2-[(aminoiminomethyl)amino]-4-thiazolyl]methyl]thio]ethyl]formamidine This compound is prepared according to Example 23, which shows the following physico-chemical characteristics:

Melting point: 87°–89° C.
One basic group (anhydrous medium): 101.2%.

| Sulphur (Schoniger): | Found | Calculated |
|---|---|---|
| | 20.3 | 21.05 |
| Elemental analysis: | C | H | N |
| Found | 42.56 | 4.70 | 17.57 |
| Calculated | 42.1 | 4.38 | 18.42 |

IR Spectrum: characteristic bands at 1740 cm$^{-1}$ (C=O, st); 1600 cm$^{-1}$ (C=N, st).

$^1$H-NMR (DMSO-d$_6$): δ=2.58 (2H, t, —S—C$\underline{H}$$_2$—CH$_2$), 3.40 (2H), m, —CH$_2$—C$\underline{H}$$_2$—NH), 3.53 (2$\underline{H}$, s, het—C$\underline{H}$$_2$—S), 3.85 (3H, s, —COOC$\underline{H}$$_3$), 6.38 (1H, s, thiazole), 6.80 (4H, wide, guanidine), 7.82–8.14 (4H, m, aromatic), 8.18 (1H, s, —NH—C$\underline{H}$=N), 9.05 (1H, wide, —NH—CH=).

EXAMPLE 25

N-p-dimethylaminobenzene-sulphonyl-N'-[2-[[[2-[(aminoiminomethyl)amino]-4-thiazolyl]methyl]thio]ethyl]formamidine This compound is prepared according to Example 23, which shows the following physico-chemical characteristics:

Melting point: 180°–182° C.
Two basic groups (anhydrous medium): 99.25%.

| Sulphur (Schoniger): | Found | Calculated |
|---|---|---|
| | 21.41 | 21.75 |
| Elemental analysis: | C | H | N |
| Found | 44.2 | 5.55 | 22.3 |
| Calculated | 43.52 | 5.27 | 22.2 |

IR Spectrum: characteristic bands at 1610 cm$^{-1}$ (C=N, st).

$^1$H-NMR (DMSO-d$_6$): δ=2.56 (2H, t, —S—C$\underline{H}$$_2$—CH$_2$), 2.95 (6H, s, —N(C$\underline{H}$$_3$)$_2$), 3.3 (2H, m, —C$\underline{H}$$_2$—CH$_2$—NH), 3.52 (2H, s, het—C$\underline{H}$$_2$—S), 6.40 (1H, s, thiazole), 6.64–7.56 (8H, m, guanidine, aromatic), 8.05 (1H, s, —NH—C$\underline{H}$=N), 8.6 (1H, wide, —N$\underline{H}$—CH=).

EXAMPLE 26

N-m-nitrobenzene-sulphonyl-N'-[2-[[[2-[(aminoiminomethyl)amino]-4-thiazolyl]methyl]thio]ethyl]formamidine This compound is prepared according to Example 23, which shows the following physico-chemical characteristics:

Melting point: 175°–177° C.
One basic group (anhydrous medium): 98.6%.

| Sulphur (Schoniger): | Found | Calculated |
|---|---|---|
| | 20.16 | 21.67 |
| Elemental analysis: | C | H | N |
| Found | 38.27 | 4.21 | 20.98 |
| Calculated | 37.91 | 3.86 | 22.11 |

IR Spectrum: characteristic bands at 1600 cm$^{-1}$ (C=N, st).

$^1$H-NMR (DMSO-d$_6$): δ=2.58 (2H, t, —S—C$\underline{H}$$_2$—CH$_2$), 3.4 (2H, m, C$\underline{H}$$_2$—CH$_2$—NH), 3.52 (2H, s, het—C$\underline{H}$$_2$—S), 6.40 (1H, s, thiazole), 6.78 (4H, wide, guanidine), 7.7–8.44 (5H, m, aromatic, —N$\underline{H}$—C$\underline{H}$=N—).

EXAMPLE 27

N-m-dimethylaminobenzene-sulphonyl-N'-[2-[[[2-[(aminoiminomethyl)amino]-4-thiazolyl]methyl]thio]ethyl]formamidine This compound is prepared according to Example 23, which shows the following physico-chemical characteristics:

Melting point: 149°–153° C.
Two basic groups (anhydrous medium): 99.3%.

| Sulphur (Schoniger): | Found | Calculated |
|---|---|---|
| | 20.81 | 21.78 |
| Elemental analysis: | C | H | N |
| Found | 42.70 | 5.52 | 22.40 |
| Calculated | 43.52 | 5.25 | 22.20 |

IR Spectrum: characteristic bands at 1610 cm$^{-1}$ (C=N, st).

$^1$H-NMR (DMSO-d$_6$): δ=2.58 (2H, t, —S—C$\underline{H}$$_2$—CH$_2$), 2.9 (6H, s, —N(C$\underline{H}$$_3$)$_2$), 3.4 (2H, m, CH$_2$—C$\underline{H}$$_2$—NH), 3.52 (2H, s, het—$\underline{C}$H$_2$—S—), 6.38 (1H, s, thiazole), 6.78–7.40 (4H, m, aromatic), 8.1 (1H, s, —NH—C$\underline{H}$=N), 8.8 (1H, wide, —N$\underline{H}$—CH—).

EXAMPLE 28

N-m-methylsulphonylbenzenepsulphonyl-N'-[2-[[[2-[(aminoiminomethyl)amino]-4-thiazolyl]methyl]thio]ethyl]formamidine This compound is prepared according to Example 23, which shows the following physico-chemical characteristics:

Melting point: 75°–85° C.
One basic group (anhydrous medium): 98.97%.

| Sulphur (Schoniger): | Found | Calculated |
|---|---|---|
| | 24.85 | 26.90 |
| Elemental analysis: | C | H | N |
| Found | 36.9 | 4.51 | 17.11 |
| Calculated | 37.80 | 4.23 | 17.63 |

IR Spectrum: characteristic bands at 1610 cm$^{-1}$ (C=N, st).

$^1$H-NMR (DMSO-d$_6$): δ=2.58 (2H, t, —S—C$\underline{H}$$_2$—CH$_2$), 3.25 (3H, s, —SO$_2$—C$\underline{H}$$_3$), 3.4 (2H, wid$\underline{e}$, CH$_2$—C$\underline{H}$$_2$—NH), 3.55 (2H, s, het—C$\underline{H}$$_2$—S), 6.4 (1H, s, thiazole), 6.80 (4H, wide, guanidine), 7.58–8.2 (4H, m, aromatic), 8.22 (1H, s, —NH—C$\underline{H}$=N), 9.1 (1H, wide, —N$\underline{H}$—CH=).

The hydrogen maleate is prepared by dissolving the base in acetone and adding the stoichiometric quantity of maleic acid dissolved in acetone. Melting point: 181°–184° C.

2 acid groups (anhydrous medium): 98.9%

| Sulphur (Schoniger): | found | calculated | |
|---|---|---|---|
| | 21.02 | 21.64 | |
| Elemental analysis: | C | H | N |
| found | 38.70 | 4.16 | 13.85 |
| calculated | 38.50 | 4.08 | 14.18 |

IR Spectrum: characteristic bands at 1690 cm$^{-1}$ (C=O, st) and 1610 (C=N, st).

$^1$H-NMR (DMSO-d$_6$): 2.58 (2H, t, S—CH$_2$—CH$_2$), 3.26 (3H, s, —SO$_2$—CH$_3$), 3.4 (2H, wide, CH$_2$—CH$_2$—NH), 3.55 (2H, s, het—CH$_2$—S), 6.06 (2H, s, —CH=CH—), 7 (1H, s, thiazole), 7.68–8.22 (5H, m, aromatic and NH—CH=N), 9.1 (1H, wide, —NH—CH=).

EXAMPLE 29

N-p-methylsulphonylaminobenzene-sulphonyl-N'-[2-[[[2-[(aminoiminomethyl)amino]-4-thiazolyl]methyl]thio]ethyl]formamidine This compound is prepared according to Example 23.

The hydrochloride is prepared by dissolving the base in absolute ethanol and adding the stoichiometric quantity of ethanol/hydrochloric acid, which shows the following physico-chemical characteristics:

Melting point: 126°–130°.

Two basic groups (anhydrous-HCl medium): 89.6%.

| Sulphur (Schoniger): | Found | Calculated | |
|---|---|---|---|
| | 22.56 | 24.28 | |
| Elemental analysis | C | H | N |
| Found | 33.94 | 4.66 | 17.94 |
| Calculated | 34.11 | 4.10 | 18.57 |

IR Spectrum: characteristic bands at 1605 cm$^{-1}$ (C=N, st).

$^1$H-NMR (DMSO-d$_6$): δ=2.6 (2H, t, S—CH$_2$—CH$_2$), 3.1 (3H, s, —SO$_2$—CH$_3$), 3.4 (2H, m, CH$_2$—CH$_2$—NH), 3.75 (2H, s, het—CH$_2$—S), 7.1 (1H, s, thiazole), 7.3–8.8 (4H, m, aromatic), 8.15 (1H, d, —NH—CH=N—), 8.35 (4H, wide, guanidine), 9.1 (1H, d, —NH—CH=), 10.3 (1H, wide, —HN—SO$_2$—CH$_3$).

The hydrogen maleate is prepared by dissolving the base in acetone and adding the stoichiometric quantity of maleic acid in acetone, which shows the following physico-chemical characteristics:

Melting point: 127°–131° C.

One basic group (anhydrous medium): 99.03%.

| Sulphur (Schoniger): | Found | Calculated | |
|---|---|---|---|
| | 20.1 | 21.10 | |
| Elemental analysis: | C | H | N |
| Found | 37.50 | 4.73 | 17.0 |
| Calculated | 37.55 | 4.15 | 16.13 |

IR Spectrum: characteristic bands at 1700 cm$^{-1}$ (C=O, st) and 1610 cm$^{-1}$ (C=N, st).

$^1$H-NMR (DMSO-d$_6$): δ=2.6 (2H, t, ,S—CH$_2$—CH$_2$), 3.1 (3H, s, —SO—CH$_3$), 3.4 (2H, m, CH$_2$—CH$_2$—NH), 3.7 (2H, s, het—CH$_2$—S), 6.1 (2H, s, —CH=CH—), 7 (1H, s, thiazole), 7.25–8.75 (4H, m, aromatic), 8.1 (5H, wide, guanidine, —NH—CH=N—), 8.9 (1H, wide, —NH—CH=).

EXAMPLE 30

N-m-methylsulphonylaminobenzene-sulphonyl-N'-[2-[[[2-[(aminoiminomethyl)amino]-4-thiazolyl]methyl]thio]ethyl]formamidine This compound is prepared according to Example 23.

The hydrogen maleate is prepared by dissolving the base in acetone and adding the stoichiometric quantity of maleic acid in acetone, which shows the following physico-chemical characteristics:

Melting point: 89°–94° C.

Two basic groups (anhydrous medium): 102.1%.

| Sulphur (Schoniger): | Found | Calculated |
|---|---|---|
| | 19.42 | 21.10 |

IR Spectrum: characteristic bands at 1690 cm$^-$(C=O, st) and 1605 cm$^{-1}$ (C=N, st).

$^1$H-NMR (DMSO-d$_6$): δ=2.56 (2H, t, S—CH$_2$, —CH$_2$), 3 (3H, s, SO$_2$—CH$_3$), 6.1 (2H, m, CH$_2$—CH$_2$—NH), 3.8 (2H, s, het—CH$_2$—S), 6.1 (2H, s, —CH=CH—), 7.05 (1H, s, thiazole), 7.45–7.6 (4H, aromatic), 8.17 (5H, wide, guanidine, —NH—CH=N), 9 (1H, wide, —NH—CH=).

EXAMPLE 31

N-p-methylthiobenzene-sulphonyl-N'-[2-[[[2-[(aminoiminomethyl)amino]-4-thiazolyl]methyl]thio]ethyl]formamidine This compound is prepared according to Example 23.

The hydrochloride is prepared by dissolving the base in absolute ethanol and adding the stoichiometric quantity of ethanol/hydrochloric acid, which shows the following physico-chemical characteristics:

Melting point: 104°–108° C.

Two acid groups (anhydrous medium): 97.9%.

| Sulphur (Schoniger): | Found | Calculated | |
|---|---|---|---|
| | 25.3 | 26.6 | |
| Elemental analysis: | C | H | N |
| Found | 35.73 | 4.89 | 16.61 |
| Calculated | 37.45 | 4.40 | 17.47 |

IR Spectrum: characteristic bands at 1610 cm$^{-1}$ (C=N, st).

$^1$H-NMR (DMSO-d$_6$): δ=2.5 (3H, s, —S—CH$_3$), 2.56 (2H, t, —S—CH$_2$—CH$_2$), 3.35 (2H, m, —CH$_2$—CH$_2$—NH), 7.05 (1H, s, thiazole), 7.3–7.7 (4H, m, aromatic), 8.1 (1H, d, —NH—CH=N—), 9 (1H, wide, NH—C=), 12.5 (1H, wide, guanidine).

EXAMPLE 32

N-p-bromobenzene-sulphonyl-N'-[3-[3-(1-piperidinylmethyl)phenoxy]propyl]formamidine To a solution of 6.2 g of 3-[3-(1-piperidinylmethyl)phenoxy]-1-propanamine (prepared according to British Pat. No. 2,023,133) in 20 ml of absolute ethanol, 7.3 g of ethyl N-p-bromobenzenesulphonyl-formimidate dissolved in 20 ml of absolute ethanol are dropwise added at room temperature. The mixture is kept under stirring for 1 hour and the ethanol is removed by distillation under reduced pressure. The resulting residue is purified by dissolving in 60 ml of ethyl acetate and 25 ml of water, then acidulated with 3N hydrochloric acid up to pH2. The organic phase is case aside and the aqueous phase is basified in the presence of 20 ml of sodium acetate with 1N sodium hydroxide up to pH8. The organic phase is washed with water, dried over magnesium sulphate and evaporated till dryness. The resulting residue is chromatographied by 60 silicagel column with chloroform-methanol (8:2) as eluent. 8.3 g of N-p-bromobenzene-sulphonyl-N'-[3-[3-(1-piperidinylmethyl)phenoxy]propyl]formamidine are obtained.

The hydrogen oxalate is prepared by mixing equimolecular

The hydrogen oxalate is prepared by mixing equimolecular quantities of the base and oxalic acid dissolved in ethanol and then left to crystallize under cooling. The product shows the following physico-chemical properties:

Melting point: 132°–140° C.
Three acid groups (anhydrous medium): 110.2%.

| Elemental analysis: | C | H | N |
|---|---|---|---|
| Found | 48.02 | 5.27 | 7.13 |
| Calculated | 49.32 | 5.17 | 7.19 |

| | Found | Calculated |
|---|---|---|
| Sulphur (Schoniger): | 5.1 | 5.49 |
| Bromine (Schoniger): | 12 | 13.67 |

IR Spectrum: characteristic bands at 1610 cm$^{-1}$ (C=N, st).

$^1$H-NMR (DMSO-d$_6$): δ=1.65 (6H, wide, piperidine), 1.8 (2H, m, —CH$_2$—CH$_2$—CH$_2$), 3 (4H, wide, piperidine), 3.35 (2H, m, —C$\underline{H}$$_2$—CH$_2$—CH$_2$—NH), 3.97 (2H, t, —CH$_2$—CH$_2$—CH$_2$—NH), 4.1$\overline{2}$ (2H, s, het—C$\underline{H}$$_2$—φ—), 7.1 (4H, m, 1,3-aromatic), 7.7 (4H, s, 1,4-aromatic), 8.15 (1H, d, —NH—C$\underline{H}$=N—), 9.3 (1H, wide —N$\underline{H}$—CH—).

EXAMPLE 33

N-p-methoxybenzene-sulphonyl-N'-[2-[[[2-[(aminoiminomethyl)amino]-4-thiazolyl]methyl]thio]ethyl]formamidine To a suspension of 3.04 g of [4-[[(2-aminoethyl)thio]-methyl]-2-thiazolyl]guanidine dihydrochloride (prepared according to U.S. Pat. No. 4,165,378) in 20 ml of absolute methanol, 13.3 ml of 1.66M methanol potassium hydroxide are added at 0° C. To the resulting suspension, 2.43 g of ethyl N-p-methozybenzenesulphonyl-formimidate in 20 ml of MeOH are added at room temperature. The remaining suspension is stirred for 3 hours at room temperature, then filtered off and the solvent is removed from the filtrate by distillation under reduced pressure. The formed residue is purified by dissolving in 40 ml of ethyl acetate and 40 ml of water, then acidulated with 3N hydrochloric acid up to pH2. The organic phase is cast aside and the aqueous phase is basified under the presence of 40 ml of ethyl acetate in saturated solution of sodium carbonate. The organic phase is washed with water, dried over magnesium sulphate and evaporated till dryness. 2.4 g of N-p-methoxybenzene-sulphonyl-N'-[2-[[[2-[(aminoiminomethyl)amino]-4-thiazolyl]methyl]thio]ethyl]formamidine are obtained. The product shows the following physico-chemical properties:

Melting point: 68°–76° C.
Two basic groups (anhydrous medium): 82.3%.

| Sulphur (Schoniger): | Found | Calculated |
|---|---|---|
| | 20.38 | 22.43 |

IR Spectrum: characteristic bands at 1610 cm$^{-1}$ (C=N, st).

$^1$H-NMR (DMSO-d$_6$): δ=2.6 (2H, t, —S—C$\underline{H}$$_2$—CH$_2$), 3.45 (2H, m, —CH$_2$—CH$_2$—NH), 3.55 (2H, s, het—C$\underline{H}$$_2$—S), 3.8 (3H, s, φ—OC$\underline{H}$$_3$), 6.35 (1H, s, thiazol), 6.$\overline{8}$ (4H, wide, guanidine), 6.9–7.7 (4H, m, aromatic), 8 (1H, o, —NH—C$\underline{H}$=N), 8.75 (1H, wide, —N$\underline{H}$—CH=).

The hydrogen maleate is prepared by dissolving the obtained product in acetone and adding the stoichiometric quantity of maleic acid in acetone, which shows the following physico-chemical properties:

Melting point: 166°–170° C.
Two basic groups (anhydrous medium): 101.9%.

| Elemental analysis: | C | H | N |
|---|---|---|---|
| Found | 41.36 | 4.68 | 15.43 |
| Calculated | 41.90 | 4.44 | 15.43 |

| Sulphur (Schoniger) | Found | Calculated |
|---|---|---|
| | 16.43 | 17.66 |

IR Spectrum: characteristic bands at 1700 cm$^{-1}$ (C=O, st); 1610 cm$^{-1}$ (C=N, st).

$^1$H-NMR (DMSO-d$_6$): δ=2.6 (2H, t, —S—C$\underline{H}$$_2$—CH$_2$), 3.45 (2H, m, —CH$_2$—CH$_2$—NH), 3.7 (2H, s, het—C$\underline{H}$$_2$—S), 3.8 (3H, s, φ—OC$\underline{H}$$_3$), 6.1 (2H, s, —CH=CH—), 6.9 (1H, s, thiazol), $\overline{6}$.95–7.7 (4H, m, aromatic), 8.1 (5H, wide, guanidine, —C$\underline{H}$=N), 8.7 (1H, wide, —N$\underline{H}$—CH=).

EXAMPLE 34

N-p-ethylbenzene-sulphonyl-N'-[2-[[[2-[(aminoiminomethyl)amino]-4-thiazolyl]methyl]thio]ethyl]formamidine To a suspension of 6.1 g of [4-[[(2-aminoethyl)thio]-methyl]-2-thiazolyl]guanidine dihydrochloride in 16 ml of absolute methanol, 26.6 ml of 1.66M methanol potassium hydroxide are added at 0° C. The resulting suspension is left under stirring for 30 minutes, then filtered off and to the filtrate 4.8 g of ethyl N-p-ethylbenzene-sulphonyl-formimidate are added at room temperature. A limpid solution turns out from which an abundant precipitate is formed along the course of 24 hours, then it is filtered off, washed with methanol and dried. 7 g of N-p-ethylbenzene-sulphonyl-N'-[2-[[[2-[(aminoiminomethy)amino]-4-thiazolyl]methyl]thio]ethyl]formamidine are obtained. The product shows the following phsyicochemical properties.

Melting point: 145°–149° C.
1 basic group: 100.4%.

| Elemental analysis: | C | H | N |
|---|---|---|---|
| Found | 44.99 | 5.23 | 19.58 |
| Calculated | 45.05 | 5.20 | 19.70 |

IR Spectrum: characteristic bands at 1610 cm$^{-1}$ (C=N, st).

¹H-NMR (DMSO-d₆): δ=1 (3H, t, φ—CH₂—CH₃), 2.5 (4H, m, φ—CH₂—CH₃, —S—CH₂—CH₂), 3.25 (2H, m, —S—CH₂—CH₂), 3.4 (2H, s, het—CH₂—S), 6.25 (1H, s, thiazol), 6.7 (4H, wide, guanidine), 7.1-7.7 (4H, m, aromatic), 8 (1H, s, —NH—CH=N), 8.7 (1H, wide, —NH—CH=).

The hydrochloride is prepared by dissolving 5 g of the base in 50 ml of water and adding the stoichiometric quantity of 1M HCl. Then the mixture is left under stirring for 1 hour and the solid is filtered off. 3.5 g of N-p-ethylbenzene-sulphonyl-N'-[2-[[[2-[(aminoiminomethyl)amino]-4-thiazolyl]methyl]thio]ethyl]formamidine hydrochloride are obtained, which shows the following physico-chemical properties:

Melting point: 80°-84° C.
2 basic groups (HCl): 96.8%.
Water (K.F.): 4.18%.

| Elemental analysis: | C | H | N |
|---|---|---|---|
| Found | 40.18 | 5.40 | 17.81 |
| Calculated | 41.50 | 5.01 | 18.15 |
| | found | calculated | |
| Sulfur (Schoniger): | 19.66 | 20.77 | |
| Chlorides: | 7.54 | 7.66 | |

IR Spectrum: characteristic bands at 1610 cm⁻¹ (C=N, st).

¹H-NMR (DMSO-d₆): δ=1 (3H, t, φ—CH₂—CH₃), 2.5 (4H, m, φ—CH₂—CH₃, —S—CH₂—CH₂), 3.3 (2H, m, —S—CH₂—CH₂), 3.55 (2H, s, het—CH₂—S), 6.9 (1H, s, thiazole), 7.1-7.6 (4H, m, aromatic), 8 (1H, d, —NH—CH=N—), 8.2 (4H, wide, guanidine), 8.9 (1H, wide, —NH—CH).

EXAMPLE 35

N-p-toluen-sulphonyl-N'-[2-[[[2-[(aminoiminomethyl amino]-4-thiazolyl]methyl]thio]ethyl]formamidine To a suspension of 10 g of [4-[[(2-aminoethyl)thio]methyl]-2-thiazolyl]guanidine dihydrochloride in 100 ml of methanol, 49.9 ml of 1.45M methanol potassium hydroxide are added at 0° C. The formed potassium chloride is filtered off and the methanol is removed by vacuum evaporation. 25 g of triethyl-orthoformate are added to the resulting crude and then heated in oil bath at 100°-120° C. for 2 hours. After this time, a distillation unit is fitted to the reaction flask and the stoichiometric quantity of ethanol is collected in the course of 1.5 hours. As the reaction is completed, the excess triethyl-orthoformate is removed by distillation under reduced pressure. The resulting residue, ethyl N-[2-[[[2-[(aminoiminomethyl)amino]-4-thiazolyl]methyl]thio]ethyl]formimidate, which does not require any purification, is used for the following step.

To the crude product composed by ethyl N-[2-[[[2-[(aminoimino-methyl)amino]-4-thiazolyl]methyl]thio]ethyl]formimidate, 5.6 g of p-toluensulfonamide in 50 ml of methanol are dropwise added under stirring and at room temperature. The mixture is kept under stirring for 1 hour at room temperature, the solvent is removed by distillation under reduced pressure, and the obtained residue is purified by 60-silicagel column chromatography. 9.8 g of N-toluen-sulphonyl-N'-[2-[[[2-[(aminoiminomethyl)amino]-4-thiazolyl]methyl]thio]ethyl]formamidine are obtained, having the same physico-chemical properties as in Example 1.

EXAMPLES 36-55

Following the steps described in Example 35, the compounds listed below are obtained.

EXAMPLE 36

N-benzenesulphonyl-N'-[2-[[[2-[(aminoiminomethyl)amino]-4-thiazolyl]methyl]thio]ethyl]formamidine, having the same physico-chemical properties as in Example 2.

EXAMPLE 37

N-methanesulphonyl-N'-[2-[[[2-[(aminoiminomethyl)amino]-4-thiazolyl]methyl]thio]ethyl]formamidine hydrogen maleate, having the same physico-chemical properties as in Example 3.

EXAMPLE 38

N-p-nitrobenzene-sulphonyl-N'-[2-[[[2-[(aminoiminomethyl)amino]-4-thiazolyl]methyl]thio]ethyl]formamidine hydrogen maleate, having the same physico-chemical properties as in Example 4.

EXAMPLE 39

N-p-chlorobenzene-sulphonyl-N'-[2-[[[2-[(aminoiminomethyl)amino]-4-thiazolyl]methyl]thio]ethyl]formamidine, having the same physico-chemical properties as in Example 5.

EXAMPLE 40

N-p-toluen-sulphonyl-N'-[2-[[[5-[(dimethylamino)methyl]-2-furanyl]methyl]thio]ethyl]formamidine, having the same physico-chemical properties as in Example 6.

EXAMPLE 41

N-p-chlorobenzene-sulphonyl-N'-[2-[[[5-[(dimethylamino)methyl]-2-furanyl]methyl]thio]ethyl]formamidine, having the same physico-chemical properties as in Example 7.

EXAMPLE 42

N-benzene-sulphonyl-N'-[2-[[[5-[(dimethylamino)methyl]-2-furanyl]methyl]thio]ethyl]formamidine, having the same physico-chemical properties as in Example 8.

EXAMPLE 43

N-methan-sulphonyl-N'-[2-[[[5-[(dimethylamino)methyl]-2-furanyl]methyl]thio]ethyl]formamidine, having the same physico-chemical properties as in Example 9.

EXAMPLE 44

N-benzene-sulphonyl-N'-[3-[3-(1-piperidinylmethyl)phenoxy]propyl]formamidine, having the same physico-chemical properties as in Example 10.

EXAMPLE 45

N-p-chlorobenzene-sulphonyl-N'-[3-[3-(1-piperidinylmethyl)phenoxy]propyl]formamidine, having the same physico-chemical properties as in Example 11.

EXAMPLE 46

N-methan-sulphonyl-N'-[3-[3-(1-piperidinylmethyl)phenoxy]propyl]formamidine, having the same physico-chemical properties as in Example 12.

EXAMPLE 47

N-p-toluen-sulphonyl-N'-[3-[3-(1-piperidinylmethyl)-phenoxy]propyl]formamidine hydrogen oxalate, having the same physico-chemical properties as in Example 13.

EXAMPLE 48

N-p-chlorobenzene-sulphonyl-N'-[2-[[(5-methyl-1H-imidazole-4-yl)methyl]thio]ethyl]formamidine, having the same physico-chemical properties as in Example 14.

EXAMPLE 49

N-benzene-sulphonyl-N'-[2-[[(5-methyl-1H-imidazole-4-yl)methyl]thio]ethyl]formamidine, having the same physico-chemical properties as in Example 15.

EXAMPLE 50

N-methan-sulphonyl-N'-[3-[3-(1-piperidinylmethyl)-phenoxy]propyl]formamidine hydrogen oxalate, having the same physico-chemical properties as in Example 17.

EXAMPLE 51

N-p-acetylaminobenzene-sulphonyl-N'-[2-[[[2-[(aminoiminomethyl)amino]-4-thiazolyl]methyl]thio]ethyl]formamidine, having the same physico-chemical properties as in Example 18.

EXAMPLE 52

N-p-acetylaminobenzene-sulphonyl-N'-[3-[3-(1-piperidinylmethyl)phenoxy]propyl]formamidine, having the same physico-chemical properties as in Example 19.

EXAMPLE 53

N-(5-acetylamino-1,3,4-thiadiazole-2-yl)sulphonyl-N'-[3-[3-(1-piperidinylmethyl)phenoxy]propyl]formamidine, having the same physico-chemical properties as in Example 20.

EXAMPLE 54

N-(5-acetylamino-1,3,4-thiadiazole-2-yl)sulphonyl-N'-[2-[[[2-[(aminoiminomethyl)amino]-4-thiazolyl]methyl]thio]ethyl]formamidine, having the same physico-chemical properties as in Example 21.

EXAMPLE 55

N-p-cartoxybenzene-sulphonyl-N'-[2-[[[2-[(aminoiminomethyl)amino]-4-thiazolyl]methyl]thio]ethyl]formamidine, potassium salt, having the sme physico-chemical properties as in Example 22.

EXAMPLE 56

N-p-bromobenzene-sulphonyl-N'-[2-[[[2-[(aminoiminomethyl]amino]-4-thiazolyl]methyl]thio]ethyl formamidine To a suspension of 10 g of [4-[[(2-aminoethyl)thio]methyl]-2-thiazolyl]guanidine dihydrochloride in 100 ml of methanol, 49.9 ml of 1.45M methanol potassium hydroxide are added at 0° C. The formed potassium chloride is filtered off and the methanol is removed by vacuum evaporation. 25 g of triethylorthoformate are added to the resulting crude and then heated in oil bath at 100°–120° C. for 2 hours. After this time, a distillation unit is fitted to the reaction flask and the stoichiometric quantity of ethanol is collected in the course of 1.5 hours. As the reaction is completed, the excess triethylorthoformate is removed by distillation under reduced pressure. The resulting residue, ethyl N-[2-[[[2-[(aminoiminomethyl)amino]-4-thiazolyl]methyl]thio]ethyl]formamidine, which does not require any purification, is used for the following step.

To the crude product composed by ethyl N-[2-[[[2-[(aminoiminomethyl)amino]-4-thiazolyl]methyl]thio]ethyl]formimidate, 7.7 g of p-bromobenzenesulfonamide in 50 ml of methanol are dropwise added under stirring and at room temperature. The mixture is kept under stirring for 1 hour at room temperature, the solvent is removed by distillation under reduced pressure, and the obtained residue is purified by 60-silicagel column chromatography. 13.5 g of N-p-bromobenzene-sulphonyl-N'-[2-[[[2-[(aminoiminomethyl)amino]-4-thiazolyl]methyl]thio]ethyl]formamidine are obtained.

Melting point: 107°–110° C.

1 basic group (anhydrous medium): 99.15%.

| Elemental analysis: | C | H | N |
|---|---|---|---|
| found | 34.18 | 3.76 | 18.00 |
| calculated | 35.22 | 3.59 | 17.60 |

| | Found | Calculated |
|---|---|---|
| Sulphur (Schoniger): | 19.11 | 20.15 |
| Bromine (Schoniger): | 15.38 | 16.74 |

IR Spectrum: characteristic bands at 1605 cm$^{-1}$ (C=N, st).

$^1$H-NMR (DMSO-d$_6$): δ=2.58 (2H, t, —S—C$\underline{H}$$_2$—CH$_2$), 3.45 (2H, m, CH$_2$—C$\underline{H}$$_2$—NH—), 3.55 (2H, s, het—C$\underline{H}$$_2$—S—), 6.4 (1H, s, thiazole), 6.8 (4H, wide, guanidine), 7.7 (4H, s, aromatic), 8.15 (1H, s, NH—C$\underline{H}$=N), 9 (1H, wide, —N$\underline{H}$—CH=).

The hydrochloride is prepared by dissolving the base in absolute ethanol and adding the stoichiometric quantity of ethanol/hydrochloric acid.

The hydrochloride is also prepared by mixing up the base with water and adding the stoichiometric quantity of 1M HCl aqueous solution, and then the resulting solution is subjected to lyophylization.

In both cases the product shows the following Nuclear Magnetic Resonance Spectrum:

$^1$H-NMR (DMSO-d$_6$): δ=2.38 (2H, t, —S—C$\underline{H}$$_2$—CH$_2$), 3.45 (2H, m, CH$_2$—C$\underline{H}$$_2$—NH), 3.7 (2H, s, het, C$\underline{H}$$_2$—S), 7.06 (1H, s, thiazole), 7.7 (4H, s, aromatic), 8.12 (1H, d, —NH—C$\underline{H}$=N), 8.32 (4H, wide, quanidine), 9.65 (1H, wide, —N$\underline{H}$—CH=), 13.15 (1H, wide, guanidine).

The methansulphonate is prepared by mixing up the base with water and adding stoichiometric quantity of 1M methansulfonic acid in water, and then the resulting solution is subjected to lyophylization.

1 basic group (anhydrous medium): 89%.

| Sulphur (Schoniger): | Found | Calculated |
|---|---|---|
| | 20.31 | 22.36 |

$^1$H-NMR (DMSO-d$_6$): δ=2.5 (3H, s, C$\underline{H}$$_3$—SO$_3$H), 2.58 (2H, t, —S—C$\underline{H}$$_2$—CH$_2$, 3.45 (2H, m, C$\underline{H}$$_2$—CH$_2$—NH), 3.7 (2H, s, het—C$\underline{H}$$_2$—S), 7.05 (1H, s, thiazole), 7.7 (4H, s, aromatic), 8.15 (1H, d, —NH—C$\underline{H}$=NH), 8.38 (4H, wide, guanidine), 9.3 (1H, wide, —N$\underline{H}$—CH=), 13.2 (1H, wide, guanidine).

EXAMPLES 57–64

Following the steps described in Example 56, the compounds listed below are obtained.

EXAMPLE 57

N-p-methoxycarbonylbenzene-sulphonyl-N'-[2-[[[2-[(aminoiminomethyl)amino]-4-thiazolyl]methyl]thio]ethyl]formamidine, having the same physico-chemical properties as in Example 24.

EXAMPLE 58

N-p-dimethylaminobenzene-sulphonyl-N'-[2-[[[2-[(aminoiminomethyl)amino]-4-thiazolyl]methyl]thio]ethyl]formamidine, having the same physico-chemical properties as in Example 25.

EXAMPLE 59

N-m-nitrobenzene-sulphonyl-N'-[2-[[[2-[(aminoiminomethyl)amino]-4-thiazolyl]methyl]thio]ethyl]formamidine, having the same physico-chemical properties as in Example 26.

EXAMPLE 60

N-m-dimethylaminobenzene-sulphonyl-N'-[2-[[[2-[(aminoiminomethyl)amino]-4-thiazolyl]methyl]thio]ethyl]formamidine, having the same physico-chemical properties as in Example 27.

EXAMPLE 61

N-m-methylsulphonylbenzene-sulphonyl-N'-[2-[[[2-[(aminoiminomethyl)amino]-4-thiazolyl]methyl]thio]ethyl]formamidine, having the same physico-chemical properties as in Example 28.

EXAMPLE 62

N-p-methylsulphonylaminobenzene-sulphonyl-N'-[2-[[[2-[(aminoiminomethyl)amino]-4-thiazolyl]methyl]thio]ethyl]formamidine hydrochloride, having the same physico-chemical properties as in Example 29.

EXAMPLE 63

N-m-methylsulphonylaminobenzene-sulphonyl-N'-[2-[[[2-[(aminoiminomethyl)amino]-4-thiazolyl]methyl]thio]ethyl]formamidine hydrogen maleate, having the same physico-chemical properties as in Example 30.

EXAMPLE 64

N-p-methylthiobenzene-sulphonyl-N'-[2-[[[2-[(aminoiminomethyl)amino]-4-thiazolyl]methyl]thio]ethyl]formamidine hydrochloride, having the same physico-chemical properties as in Example 31.

EXAMPLE 65

N-p-bromobenzene-sulphonyl-N'-[3-[3-(1-piperidinylmethyl)phenoxy]propyl]formamidine A suspension of 8.2 g of 3-[3-(1-piperidinylmethyl)-phenoxy]-1-propanamine (prepared according to British Pat. No. 2,023,133) in 25 ml of triethyl-orthoformate are heated in oil bath at 100°–120° C. for 2 hours. After this time, a distillation unit is fitted to the reaction flask and the stoichiometric quantity of ethanol is collected in the course of 1.5 hours. As the reaction is completed, the excess triethyl-orthformate is removed by distillation under reduced pressure. The resulting residue, ethyl N-[3-[3-(1-piperidinylmethyl)phenoxy]propyl]formimidate, which does not require any purification, is used for the following step.

To the crude product composed by ethyl N-[3-[3-(1-piperidinylmethyl)phenoxy]propyl]formimidate, 7.7 g of p-bromobenzenesulfonamide in 50 ml of methanol are dropwise added under stirring and at room temperature. The mixture is kept under stirring for 1 hour at room temperature, the solvent is removed by distillation under reduced pressure, and the obtained residue is purified by 60-silica gel column chromatography. 14.0 g of N-p-bromobenzene-sulphonyl-N'-[3-[3-(1-pipidinylmethyl)phenoxy]propyl]formamidine.

The hydrogen oxalate is prepared according to Example 32.

EXAMPLES 66–67

Following the steps described in Example 65, the compounds listed below are obtained.

EXAMPLE 66

N-p-methoxybenzene-sulphonyl-N'-[2-[[[2-[(aminoiminomethyl)amino]-4-thiazolyl]methyl]thio]ethyl]formamidine, having the same physico-chemical properties as in Example 33.

EXAMPLE 67

N-p-ethylbenzene-sulphonyl-N'-[2-[[[2-[(aminoiminomethyl)amino]-4-thiazolyl]methyl]thio]ethyl]formamidine, having the same physico-chemical properties as in Example 34.

While the invention has been described and illustrated as embodied in sulfonamidines, processes for their production and pharmaceutical compositions containing the same, it is not intended to be limited to the embodiments described, and various modifications and structural changes may be made without departing in any way from the spirit of the present invention.

Without further ado, the foregoing will so fully reveal the gist of the present invention that others can, by applying current knowledge, readily adapt it for various applications without omitting features that, from the standpoint of prior art, fairly constitute the essential characteristics of the present invention.

What is claimed as new and desired to be protected by Letters Patent is set forth in the appended claims:

1. A compound of the formula (I):

$$R-NH-CH=N-SO_2-R_1 \qquad (I)$$

wherein R is a group selected from 2-[[(5-methyl-1H-imidazole-4-yl)methyl]thio]ethyl, 2-[[[5-[(dimethylamino)methyl]-2-furanyl]methyl]thio]ethyl, 2-[[[2-[(aminoiminomethyl)amino]-4-thiazolyl]methyl]thio]ethyl or 3-[3-(1-piperidinylmethyl)phenoxy propyl and $R_1$ is lower alkyl having 4 carbon atoms at most, phenyl optionally substituted by lower alkyl having 4 carbon atoms at most, halogen, nitro, lower alkoxy having 4 carbon atoms at most, lower alkanoylamino having 4 carbon atoms at most, carboxylic acid, lowr alkoxycarbonyl the alkoxy group of which having 4 carbon atoms at most, lower dialkylamino the alkyl groups of which having 4 carbon atoms each at most, lower alkylsulphonyl the alkyl group of which having 4 carbon atoms at most, lower alkylsulphonylamino the alkyl group of which having 4 carbon atoms at most, lower alkylthio the alkyl group of which having 4 carbon atoms at most or 1,3,4-thiadiazole-2-yl, with or without being substituted by lower alkanoylamino having 4 carbon atoms at most and the pharmaceutically acceptable salts thereof.

2. The compound of claim 1, wherein $R_1$ is methyl.

3. The compound of claim 1, wherein $R_1$ is phenyl optionally substituted by a group selected from methyl, ethyl, chlorine, bromine, nitro, methoxy, acetylamino, carboxylic acid, methoxycarbonyl, dimethylamino, methylsulphonyl, methylsulphonylamino or methylthio.

4. The compound of claim 1, wherein $R_1$ is 5-acetylamino-1,3,4-thiadiazole-2-yl.

5. Process for preparing a compound of formula (I) according to claim 1, comprising reacting an amine of formula (II):

$$R-NH_2 \quad (II)$$

wherein R is as defined in (I), with an intermediate of formula (III):

$$R_2O-CH=N-SO_2-R_1 \quad (III)$$

wherein $R_2$ is lower alkyl having 4 carbon atoms at most and $R_1$ is as defined in (I), in a medium selected from an alkanol having 1 to 4 carbon atoms.

6. Process for preparing a compound of formula (I) according to claim 1, comprising reacting an amine of formula (II):

$$R-NH_2 \quad (II)$$

wherein R is as defined in (I), which excess orthoformate of formula (III'):

$$H-C(OR_2)_3 \quad (III')$$

wherein $R_2$ is lower alkyl having 4 carbon atoms at most, thus obtaining the intermediate imidate of formula (IV):

$$R-N=CH-OR_2 \quad (IV)$$

wherein R and $R_2$ are as defined above and reacting with a sulfonamide of formula (V):

$$H_2N-SO_2-R_1 \quad (V)$$

wherein $R_1$ is as defined in (I), in a medium selected from an alkanol having 1 to 4 carbon atoms.

7. The process according to claim 5, wherein $R_2$ is ethyl.

8. The process according to claim 6, wherein $R_2$ is ethyl.

9. The process according to claim 5, wherein the alkanol is selected from methanol or ethanol.

10. The process according to claim 6, wherein the alkanol is selected from methanol or ethanol.

11. The process according to claim 5 comprising forming salts of a compound of formula (I) in an inert medium selected from water, an alkanone or an alkanol having 4 carbon atoms at most or mixtures thereof the same with water, and when the carboxylic acid is found in (I), their precursors salified with alkaline metals are generally used as starting material, thus directly obtaining the alkaline salts thereof.

12. The process according to claim 6 comprising forming salts of a compound of formula (I) in an inert medium selected from water, an alkanone or an alkanol having 4 carbon atoms at most or mixtures thereof the same with water, and when the carboxylic acid is found in (I), their precursors salified with alkaline metals are generally used as starting material, thus directly obtaining the alkaline salts thereof.

13. The process according to claim 11, wherein the alkanone is acetone.

14. The process according to claim 12, wherein the alkanone is acetone.

15. The process according to claim 11, wherein the alkanol is ethanol.

16. The process according to claim 12, wherein the alkanol is ethanol.

17. The intermediate imidate of the formula (IV), according to claim 6.

18. A pharmaceutical composition useful for the inhibition of gastric acid secretion which comprises an $H_2$-receptor blocking-effective amount of a compound according to claim 1, in admixture with a pharmaceutically acceptable excipient.

* * * * *